(12) United States Patent
Morrissey et al.

(10) Patent No.: US 10,849,747 B2
(45) Date of Patent: Dec. 1, 2020

(54) INTEGRATED SHEATH INTERFACE FEATURE

(71) Applicant: St. Jude Medical, Cardiology Division, Inc., St. Paul, MN (US)

(72) Inventors: Michael Shane Morrissey, St. Paul, MN (US); Tyler Govek, St. Paul, MN (US); John Matejka, Crystal, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 235 days.

(21) Appl. No.: 15/973,761

(22) Filed: May 8, 2018

(65) Prior Publication Data

US 2018/0325668 A1 Nov. 15, 2018

Related U.S. Application Data

(60) Provisional application No. 62/504,017, filed on May 10, 2017.

(51) Int. Cl.
*A61F 2/24* (2006.01)
*A61F 2/966* (2013.01)

(52) U.S. Cl.
CPC .......... *A61F 2/2436* (2013.01); *A61F 2/2418* (2013.01); *A61F 2/966* (2013.01); *A61F 2250/0039* (2013.01)

(58) Field of Classification Search
CPC ...... A61F 2/2436; A61F 2/2418; A61F 2/966; A61F 2/962; A61F 2/95; A61F 2002/9665
See application file for complete search history.

(56) References Cited

U.S. PATENT DOCUMENTS

| | | | |
|---|---|---|---|
| 5,628,755 A | 5/1997 | Heller et al. | |
| 5,776,140 A | 7/1998 | Cottone | |
| 8,998,970 B2 | 4/2015 | Arbefeuille et al. | |
| 9,220,617 B2 | 12/2015 | Berra | |
| 9,271,856 B2 | 3/2016 | Duffy et al. | |
| 9,433,521 B2 | 9/2016 | Deshmukh et al. | |
| 9,717,595 B2 | 8/2017 | Costello et al. | |
| 2011/0015616 A1 | 1/2011 | Straubinger et al. | |

(Continued)

OTHER PUBLICATIONS

International Search Report for PCT/US2018/031470 dated Aug. 3, 2018, 4 pages.

*Primary Examiner* — Katrina M Stransky
(74) *Attorney, Agent, or Firm* — Lerner, David, Littenberg, Krumholz & Mentlik, LLP

(57) ABSTRACT

A delivery device for an implantable medical device includes an inner shaft with a device-carrying region, an outer shaft surrounding the inner shaft, a sheath at a distal end of the outer shaft, and a sleeve. The outer shaft is movable relative to the inner shaft from an advanced position in which the sheath surrounds the device-carrying region to a retracted position in which the sheath exposes the device-carrying region. The sheath includes a proximal structure having a cylindrical portion between first and second transition zones. The sleeve surrounds the outer shaft and is movable relative to the outer shaft from an advanced position in which a distal end portion of the sleeve surrounds the cylindrical portion to a retracted position in which the distal end portion of the sleeve is spaced proximally from the cylindrical portion.

20 Claims, 7 Drawing Sheets

(56) References Cited

U.S. PATENT DOCUMENTS

| | | | |
|---|---|---|---|
| 2013/0178930 A1* | 7/2013 | Straubinger | A61F 2/2436 623/2.1 |
| 2014/0005768 A1* | 1/2014 | Thomas | A61F 2/2436 623/2.11 |
| 2014/0031922 A1 | 1/2014 | Duffy et al. | |
| 2015/0142097 A1* | 5/2015 | Coverdale | A61F 2/95 623/1.12 |
| 2015/0238315 A1 | 8/2015 | Rabito et al. | |
| 2017/0325953 A1 | 11/2017 | Klima et al. | |

* cited by examiner

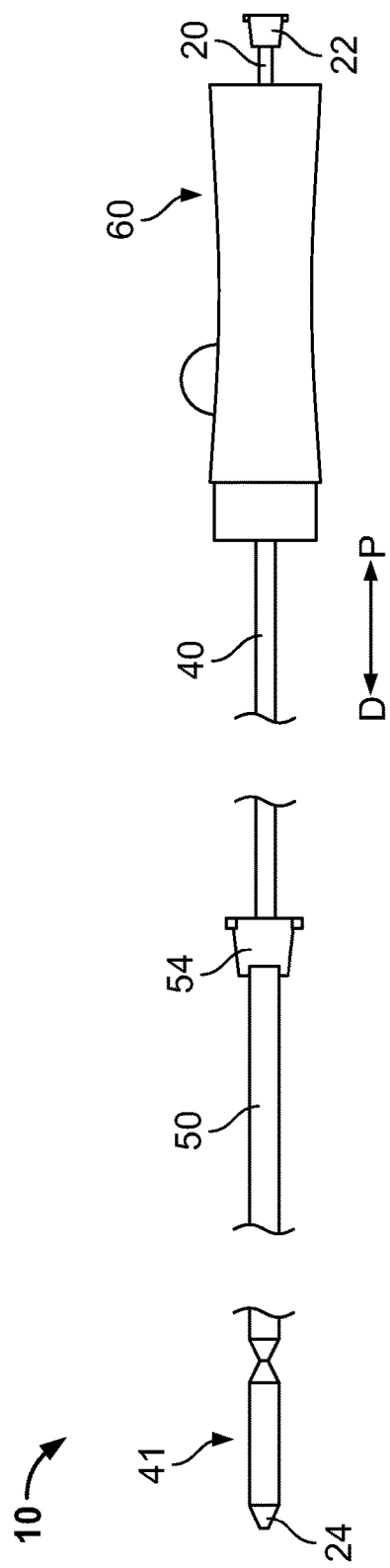
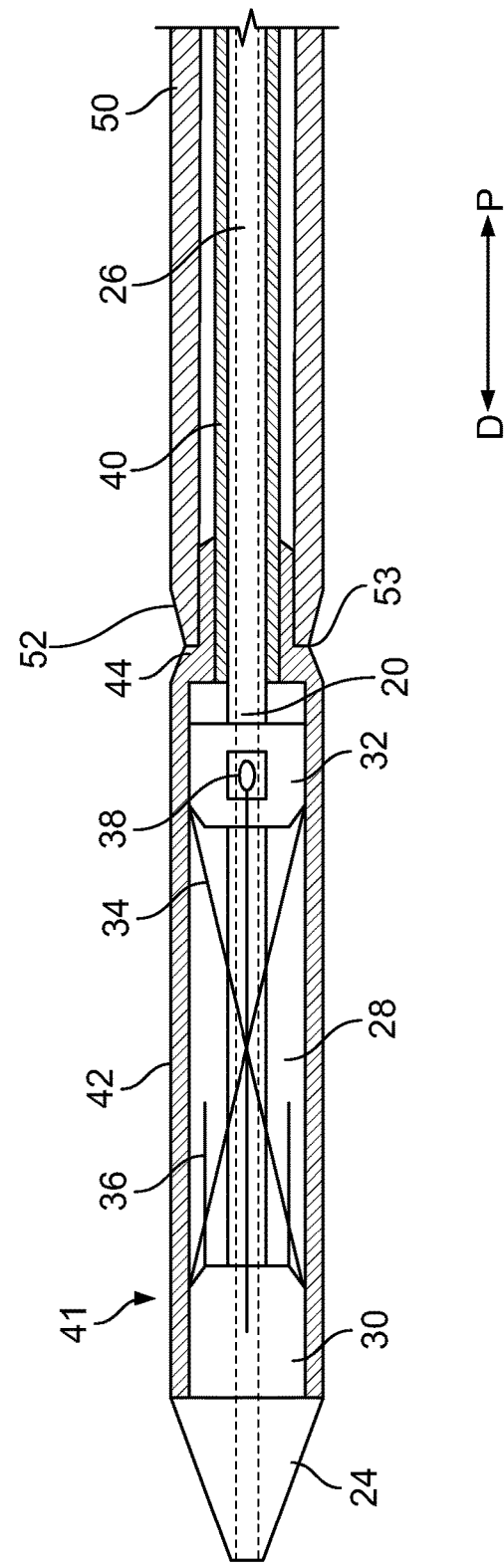
FIG. 1
FIG. 2

INTEGRATED SHEATH INTERFACE FEATURE

The present application claims the benefit of the filing date of U.S. Provisional Patent Application No. 62/504,017, filed May 10, 2017, the disclosure of which is hereby incorporated by reference herein.

BACKGROUND OF THE DISCLOSURE

The present disclosure relates to systems and methods for implanting a medical device within the cardiovascular system of a subject such as a human patient.

Medical devices such as prosthetic heart valves and stents commonly are inserted by a transluminal insertion procedure. One such procedure uses a delivery system including an inner shaft surrounded by an outer shaft. The implantable device is carried on the inner shaft near a distal end of the shaft. The outer shaft has a sheath at its distal end. A proximal end of the inner shaft is fixed to a handle. The outer shaft may be connected to a mechanism within the body of the handle. The mechanism normally holds the outer shaft in fixed position relative to the handle body, but can be actuated by a control element, such as a thumb wheel, lever or the like provided on the handle to move the outer shaft and the sheath in the proximal and distal directions relative to the inner shaft.

To introduce the delivery system into a patient, a guidewire is placed into the subject's vasculature through an entry point where a blood vessel can be accessed conveniently. For example, where a device is to be implanted in or near the heart, the entry point may be at the femoral artery in the subject's groin. A hollow cannula referred to as an introducer is provided around the guidewire at the entry point. The introducer cannula typically incorporates an elastomeric seal to limit blood loss during the procedure.

The implantable device is loaded onto the inner shaft of the delivery system, and the sheath and outer shaft are moved to an advanced position at which the sheath covers the device. The delivery system is then advanced over the guidewire and through the elastomeric seal of the introducer and into the subject's vasculature. The delivery system is advanced through the vasculature until the device is disposed at the desired implantation site. For example, the physician may determine that the delivery system is positioned properly by observing the subject under fluoroscopic imaging and determining that an alignment marker on the delivery system or the implantable device is disposed at the proper location relative to the subject's anatomy. Once the delivery system is at the proper location, the physician attempts to hold the handle stationary while actuating the control element of the handle to retract the outer shaft and the sheath proximally relative to the inner shaft and the device. When the implantable device includes a self-expanding stent, the device will expand as the sheath is retracted. This action ultimately detaches the device from the delivery system and implants it in the subject.

In such a procedure, the delivery system must bend to follow the path of the guidewire through the subject's vasculature. For example, when a prosthetic heart valve is to be delivered through the femoral artery to the vicinity of the aortic annulus of the heart, the distal end of the delivery system must bend around the arch of the aorta. To allow sufficient flexibility, the outer shaft typically has a diameter smaller than the diameter of the sheath. For example, for the implantation of some prosthetic heart valves, the sheath may have a size of about 18 French (about 6 mm diameter) to provide sufficient space to accommodate the valve in its collapsed condition, whereas the outer shaft has a size of about 14 French (about 4.67 mm diameter). To provide reasonable sealing against blood loss, the elastomeric seal in the introducer sheath must be sufficiently resilient to accommodate these different diameters as they are passed through the seal. On the other hand, friction between the seal and the outer shaft impedes the advancing motion of the delivery system. Moreover, when the physician actuates the control element on the handle to move the outer shaft and sheath relative to the inner shaft, the friction between the introducer and the outer shaft tends to hold the outer shaft stationary relative to the subject. Thus, the handle and the inner shaft tend to move relative to the subject while the device is being exposed. This displaces the device from the desired position.

Certain delivery systems disclosed in U.S. Published Patent Application No. 2014/0005768 A1, the disclosure of which is hereby incorporated by reference herein, incorporate a sleeve that fits around the outside of the outer shaft. The sleeve has an inner diameter just slightly larger than the outer diameter of the outer shaft to provide a close but freely slideable fit. Such a device can be used in the same manner as discussed above. When the control element is actuated, however, the outer shaft slides freely relative to the inner shaft to release the implantable device without displacing it from its intended position. When the implantable device is properly positioned, and the delivery system is advanced through the introducer, the sleeve stops at the introducer so that the sleeve seals against the elastomeric seal. Nonetheless, still further improvements to the delivery system are desirable.

BRIEF SUMMARY

According to one aspect of the disclosure, a delivery device for an implantable medical device includes an elongated inner shaft having a distal end and a device-carrying region adjacent the distal end. An elongated, hollow outer shaft surrounds the inner shaft, the outer shaft having a distal end and being slideable relative to the inner shaft. A sheath is positioned at the distal end of the outer shaft and is slideable with the outer shaft. A main portion of the sheath has an outside diameter greater than an outside diameter of the outer shaft. The outer shaft is movable relative to the inner shaft in a proximal direction from an advanced position in which the sheath surrounds the device-carrying region of the inner shaft to a retracted position in which the sheath exposes the device-carrying region. The sheath has a proximal structure including a cylindrical portion, a first transition zone extending between the outer shaft and the cylindrical portion, and a second transition zone extending between the cylindrical portion and the main portion of the sheath. A sleeve surrounds a portion of the outer shaft and is moveable relative to the outer shaft from an advanced position in which a distal end portion of the sleeve surrounds the cylindrical portion of the proximal structure of the sheath to a retracted position in which the distal end of the sleeve is spaced proximally from the cylindrical portion of the proximal structure of the sheath.

BRIEF DESCRIPTION OF THE DRAWINGS

FIG. 1 is a highly schematic elevational view of a delivery system according to one embodiment of the disclosure.

FIG. 2 is a cross-sectional view of the distal end of the delivery system shown in FIG. 1.

DETAILED DESCRIPTION

The terms "distal" and "distally" as used in this disclosure with reference to a delivery system means the end of the delivery system which is first inserted into the patient, i.e., the leading end of the delivery system farthest from the user, and the direction towards the leading end. The terms "proximal" and "proximally" have the opposite meaning, namely the trailing end of the delivery system closest to the user, and the direction towards the trailing end. The proximal and distal directions are indicated in the figures by the arrows "P" and "D" respectively. As used herein, the terms "generally," "substantially," and "about" are intended to mean the slight deviations from absolute are included within the scope of the term so modified. Like numbers refer to similar or identical elements throughout.

Figure 4:
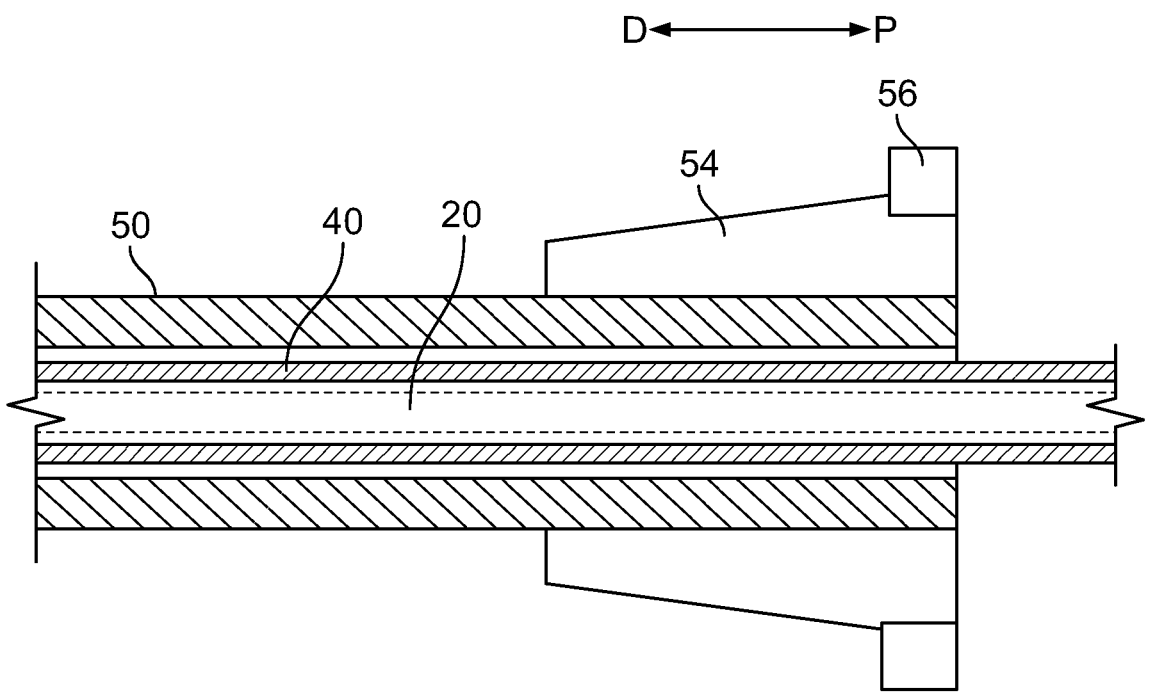
FIGS. 4 and 5 are highly schematic cross-sectional views of portions of the delivery system shown in FIG. 1.

Referring to FIGS. 1-2, a delivery device 10 according to one embodiment of the disclosure includes an inner shaft 20 having a hub 22 at its proximal end and an atraumatic tip 24 at its distal end. Tip 24 has a generally frustoconical shape with a diameter larger than the diameter of inner shaft 20 at its proximal end and tapers inwardly in the distal direction. Inner shaft 20 has a lumen 26 depicted in broken lines in FIGS. 2, 4 and 5 extending along its entire length. A device-carrying region 28 of inner shaft 20 is positioned just proximal to tip 24. Desirably, inner shaft 20 is provided with features such as a pair of collars 30 and 32 in device-carrying region 28. Although two collars 30, 32 are shown, it should be understand that a single collar may be provided, for example only proximal collar 32. These collars may be provided with features adapted to hold a collapsible implantable device in place relative to inner shaft 20 and prevent the device from moving proximally or distally relative to the inner shaft while the device is in a collapsed condition. The particular implantable device depicted in FIG. 2 is a prosthetic heart valve assembly including a stent 34 and valve leaflets 36 attached to the stent. In the particular example shown, a tab 38 on stent 34 is received in a pocket in the proximal collar 32 of inner shaft 20 so that the stent cannot move proximally or distally relative to the collar and relative to the inner shaft while the stent remains in the collapsed condition. Other arrangements can be used. For example, one or both of collars 30, 32 may incorporate projections that engage in spaces between elements of the stent. Also, elements such as sutures can be used to hold the implantable device in place relative to inner shaft 20.

An elongated outer shaft 40 surrounds inner shaft 20 over most of the length of the inner shaft. Outer shaft 40 is substantially in the form of a cylindrical tube of constant inside and outside diameters. Outer shaft 40 forms a close but freely slideable fit with inner shaft 20. A hollow sheath 41 is mounted to the distal end of outer shaft 40. Sheath 41 includes a main portion 42, which is a tube of substantially constant inside and outside diameters. The inside diameter of main portion 42 is sufficient to accommodate the features of the device-carrying region 28 of inner shaft 20, including collars 30 and 32, and to also accommodate the implantable device in the collapsed state shown in FIG. 2. The outside diameter of main portion 42 is larger than the outside diameter of shaft 40.

Figure 3:
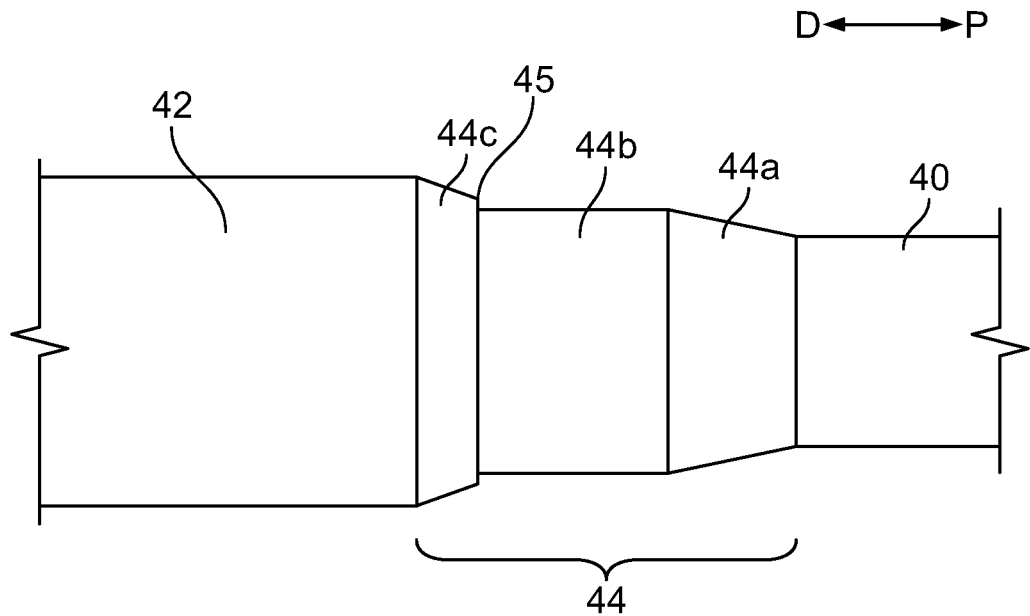
FIG. 3 is an enlarged side view of a portion of the delivery system shown in FIG. 1.

The main portion 42 of sheath 41 is open at its distal end. Sheath 41 has a substantially closed proximal structure 44 that tapers in the proximal direction from the outside diameter of main portion 42 to a diameter equal to the diameter of outer shaft 40. Sheath 41 is fixed in position at the distal end of outer shaft 40. For example, sheath 41 may be formed integrally with outer shaft 40 or may be bonded to the outer shaft by gluing, solvent welding, or the like. FIG. 3 illustrates the transition between outer shaft 40 and the main portion 42 of sheath 41. The proximal structure 44 of sheath 41 may include a proximal transition zone 44a, a landing zone 44b, and a distal transition zone 44c, each of which has an outer surface that is coaxial with the longitudinal axis of outer shaft 40. Transition zone 44a may have a proximal end with an outer diameter equal to the outer diameter of outer shaft 40, and an outer surface that is a surface of revolution defining a cone or a frustum of a cone that increases in diameter in a proximal-to-distal direction. Landing zone 44b has a cylindrical outer surface extending from the distal end of proximal transition zone 44a to the proximal end of distal transition zone 44c, with an outer diameter of substantially equal to the inner diameter of a tubular sleeve 50, described in greater detail below. Distal transition zone 44c may also have an outer surface that is a surface of revolution defining a cone or a frustum of a cone increasing in diameter in a proximal-to-distal direction to the diameter at the distal end of the distal transition zone equal to the diameter of the main portion 42 of sheath 41. The transition between proximal transition zone 44a and landing zone 44b may be substantially smooth. On the other hand, in some embodiments the transition between landing zone 44b and distal transition zone 44c may be abrupt, such that the proximalmost end of distal transition zone 44c forms a substantially flat annular rim 45 facing in the proximal direction. In other words, the proximalmost portion of distal transition zone 44c may have a diameter that is larger than the diameter of landing zone 44b. As will be explained below, this configuration enables the distal end of tubular sleeve 50 to be advanced over the proximal structure 44 of sheath 41 until it contacts rim 45. However, in other embodiments, the transition between landing zone 44b and distal transition zone 44c may be smooth.

Referring back to FIGS. 1-2, elongated tubular sleeve 50 surrounds outer shaft 40 over a portion of the length of the outer shaft. Sleeve 50 may alternately be referred to herein as an integrated sheath. The inner bore of sleeve 50 may be substantially cylindrical with a diameter that is substantially equal to the outer diameter of the landing zone 44b of the proximal structure 44 of the main portion 42 of sheath 41. With this configuration, a small annular space remains between the outer surface of outer shaft 40 and the inner bore of sleeve 50, such that sleeve 50 is freely slideable on the outer shaft. A hub 54 on the proximal end of sleeve 50 may be used to connect sleeve 50 to the handle 60 of delivery device 10, as will be described below. The majority of sleeve 50 has an outer diameter that is equal or substantially equal to the outside diameter of the main portion 42 of sheath 41. At its distal end, however, sleeve 50 has an end portion 52 with a surface concentric with the longitudinal axis of sleeve 50 and defining a cone or a frustum of a cone tapering in the distal direction. The taper of sleeve 50 may be such that the distalmost end of the sleeve has a diameter substantially equal to the diameter of the proximalmost portion of distal transition zone 44c. The distalmost end of sleeve 50 abuts the rim 45 of distal transition zone 44c when the sleeve is in its advanced position, forming a narrow abutment zone 53 where the two elements come together. In this position, sleeve 50 and sheath 41 cooperatively define an outer surface which smoothly tapers inwardly from the diameter of sheath main portion 42 to a smaller diameter in abutment zone 53 and then outwardly from the abutment zone to the larger diameter of the main portion of sleeve 50. Desirably, there are few or no abrupt changes in diameter at the abutment zone 53 between the distal end portion of sleeve 50 and the proximal end of distal transition zone 44b of sheath 41. In other words, the distal end portion of sleeve 50 and the proximal end of distal transition zone 44b may cooperatively define smooth exterior surface such that any abrupt changes in diameter are on the order of less than 1 mm and desirably less than 50 microns.

Figure 5:
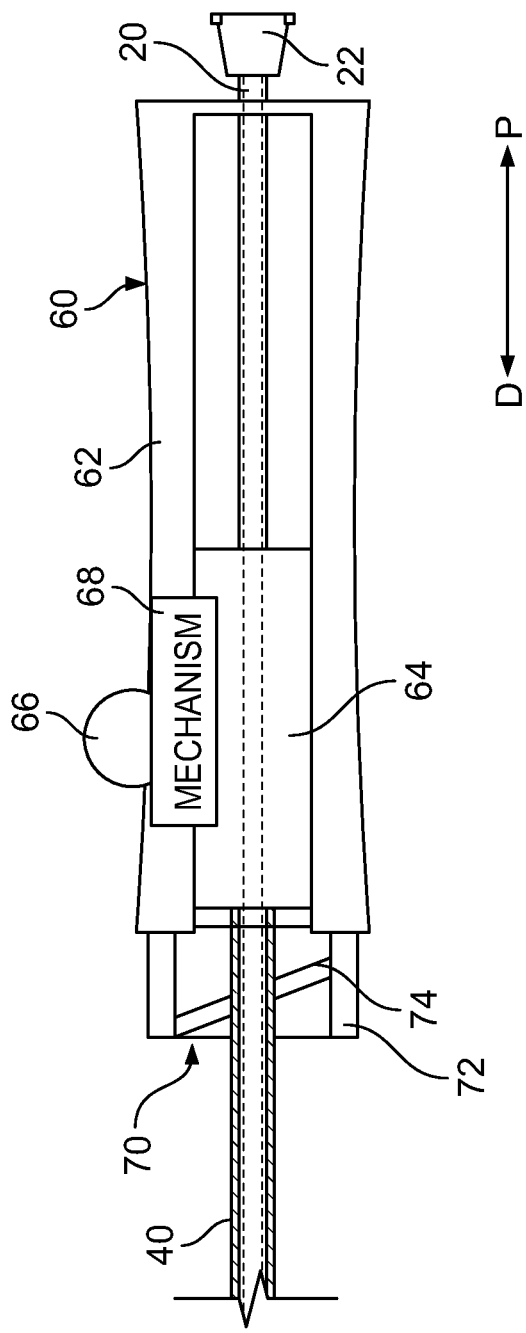

The handle 60 of delivery device 10, best seen in FIG. 5, may include a housing 62 and a carriage 64 movable longitudinally within the housing in the proximal and distal directions. The handle may have a first control element, schematically shown at 66, which may be mounted to the housing so as to be accessible to the user, as well as a mechanism 68 for moving the carriage 64 responsive to operation of the control element by the user. For example, in one embodiment, mechanism 68 may include screw threads (not shown) on the carriage 64 and a nut (not shown) surrounding the carriage in engagement with the threads. Control element 66 may include a ring surrounding the nut and exposed at one or more locations through housing 62, so that the user can turn the nut. The nut may be a "split" nut that can be closed to engage the threads or opened to disengage from the threads, and an additional control (not shown) may be provided for opening and closing the nut. A further control element (not shown) may be provided to enable the user to freely slide carriage 64 without using mechanism 68. Desirably, while mechanism 68 is engaged with carriage 64, the carriage is locked against displacement by loads applied directly to the carriage in the proximal and distal directions, and can only be moved by actuation of control element 66. Many other mechanisms are known in the art for moving a carriage within the housing of a handle responsive to operation of a control element. These include mechanical linkages such as rack and gear mechanisms, lever systems and the like. Still other mechanisms incorporate pneumatic, hydraulic, or electrical elements for moving the carriage. Any such mechanism can be used to move carriage 64. Inner shaft 20 extends through housing 62 and may extend through carriage 64. While inner shaft 20 may be fixedly attached to housing 62, for example adjacent the proximal end of the inner shaft, it is not fixedly attached to carriage 64, but rather is freely slideable relative thereto. The proximal end of outer shaft 40, on the other hand, may be fixedly attached to carriage 64. Thus, by actuating control element 66 to move carriage 64, the user can move outer shaft 40 and sheath 41 relative to handle housing 62 and relative to inner shaft 20.

Figure 6:
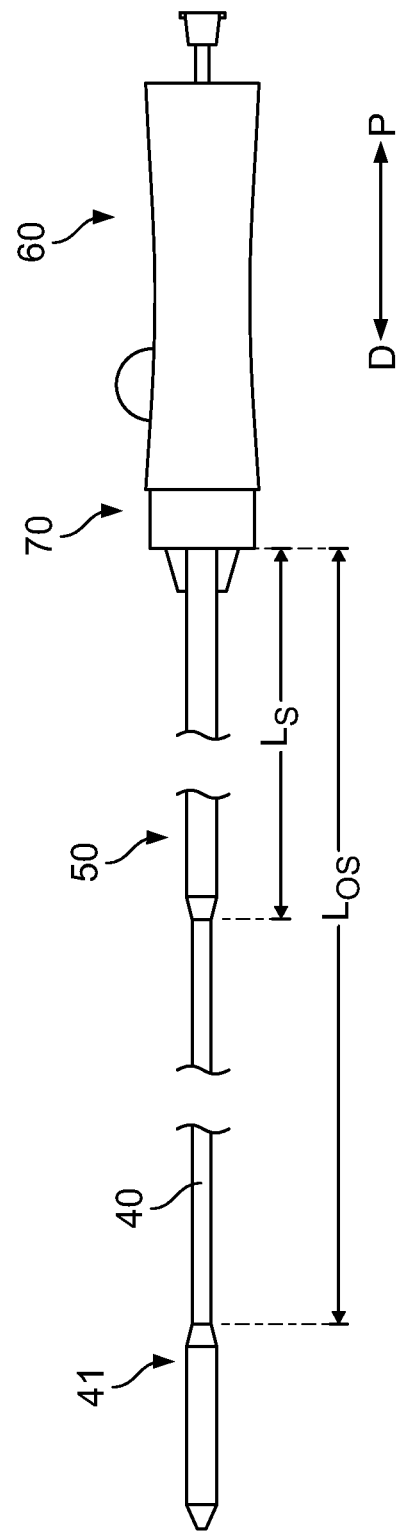
FIGS. 6 and 7 are views similar to FIG. 1, but depicting the delivery system of FIG. 1 in different operating conditions.

A catch 70 at the distal end of handle 60 includes a hollow collar 72 fixed to housing 62. Collar 72 has internal threads 74 sized to threadedly engage external threads or projections 56 on the hub 54 of sleeve 50 to thereby connect sleeve 50 to handle 60. The hub 54 of sleeve 50 can be interlocked with catch 70 when the sleeve is in a fully retracted position, as depicted in FIG. 6. However, it should be understood that catch 70 is optional and need not be provided on handle 60. Sleeve 50 can also be brought to any intermediate position between the fully advanced position of FIG. 1 and the fully retracted position of FIG. 6. While sleeve 50 is in the fully retracted position or in a partially retracted position, at which the distal end of the sleeve is spaced from sheath 41, the sheath may be retracted proximally relative to inner shaft 20 by actuating control element 66 to move carriage 64 proximally, and with it outer shaft 40 and sheath 41. In the fully retracted position of sheath 41 shown in FIG. 7, the device-carrying region 28 of inner shaft 20 is exposed and the device can expand fully so as to free itself from its engagement with the inner shaft.

Figure 8:
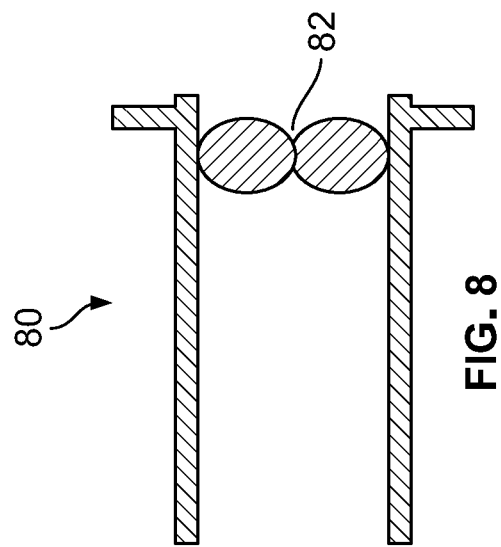
FIG. 8 is a highly schematic cross-sectional view of an introducer that may be used with the delivery system of FIG. 1.

Delivery device 10 optionally can be used in conjunction with an introducer 80, shown in FIG. 8. Introducer 80 is a tubular cannula having a resilient elastomeric seal 82 mounted therein, preferably near the proximal or inlet end of the cannula. Seal 82 may be of any form, such as a slit sheet of rubber or other elastic material, or an O-ring or other gasket capable of providing a substantially blood-tight seal between the introducer and sleeve 50. Desirably, the hub 54 of sleeve 50 is dimensioned so that it cannot pass into or through the introducer.

Figure 7:
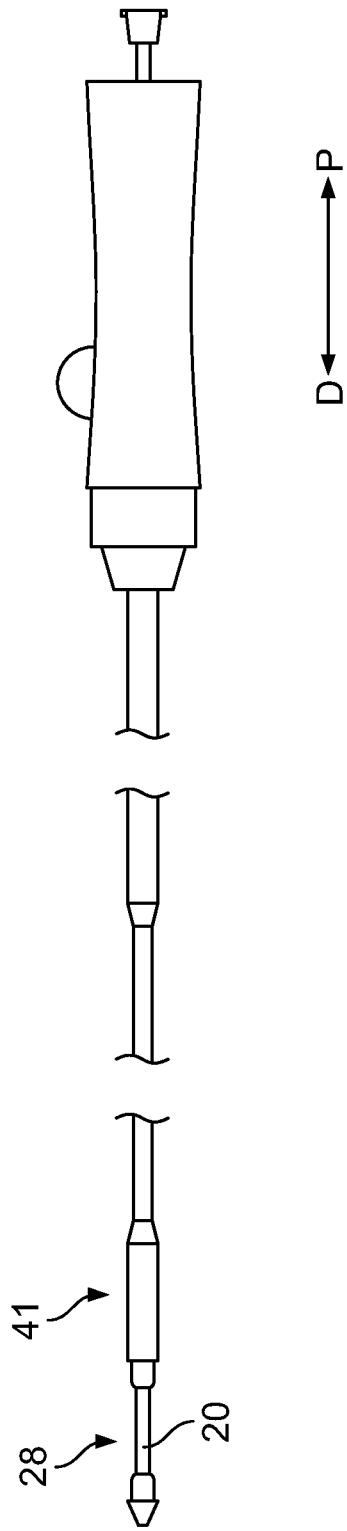

Sleeve 50 is shorter than outer shaft 40. For example, when sleeve 50 is in its fully retracted position and engaged with catch 70, and when sheath 41 and outer shaft 40 are in the advanced position shown in FIG. 6, the length $L_S$ of the sleeve projecting from the distal end of handle 60 and catch 70 may be about 15 cm less than the length $L_{OS}$ of outer shaft 40 between the most distal point of handle 60 or catch 70 and annular rim 45 on the proximal structure 44 of sheath 41; and more preferably between about 20 cm and about 40 cm less than this length. Thus, in the condition depicted in FIG. 6, the distal end of sleeve 50 desirably is at least about 15 cm proximal of sheath 41, and more preferably about 20 cm to about 40 cm proximal of the sheath. This spacing is substantially greater than the distance through which sheath 41 moves from the advanced position (FIG. 6) to the retracted position (FIG. 7). In one embodiment intended for placement of a valve in the aortic annulus of an adult human, the length $L_S$ of sleeve 50 may be on the order of 70 cm, whereas the relevant length $L_{OS}$ of outer shaft 40 may be on the order of 100 cm. Sleeve 50 and the main portion 42 of sheath 41 may have a size of about 18 French (6 mm) diameter, whereas outer shaft 40 may have a size of about 14 French (4.67 mm diameter). Alternative catches and handles may be suitable for use with delivery device 10, for example those described in U.S. Patent Publication No. 2017/0325953, the disclosure of which is hereby incorporated by reference herein. Further, as noted above, handle 60 may be provided without catch 70 or any similar catch mechanism. In those embodiments, hub 54 may be left in a position adjacent the access site in the patient during the procedure, without locking hub 54 to handle 60.

Inner shaft 20, outer shaft 40, sleeve 50 and sheath 41 can be formed from medically acceptable polymeric materials. Desirably, the materials are selected so that inner shaft 20 and outer shaft 40 have sufficient flexibility to accommodate the tortuous paths encountered in use, and to provide low-friction, easily slideable engagement between the inner and outer shafts and between the outer shaft and sleeve 50. Sleeve 50 may be somewhat stiffer than inner shaft 20 and outer shaft 40.

Figure 9:
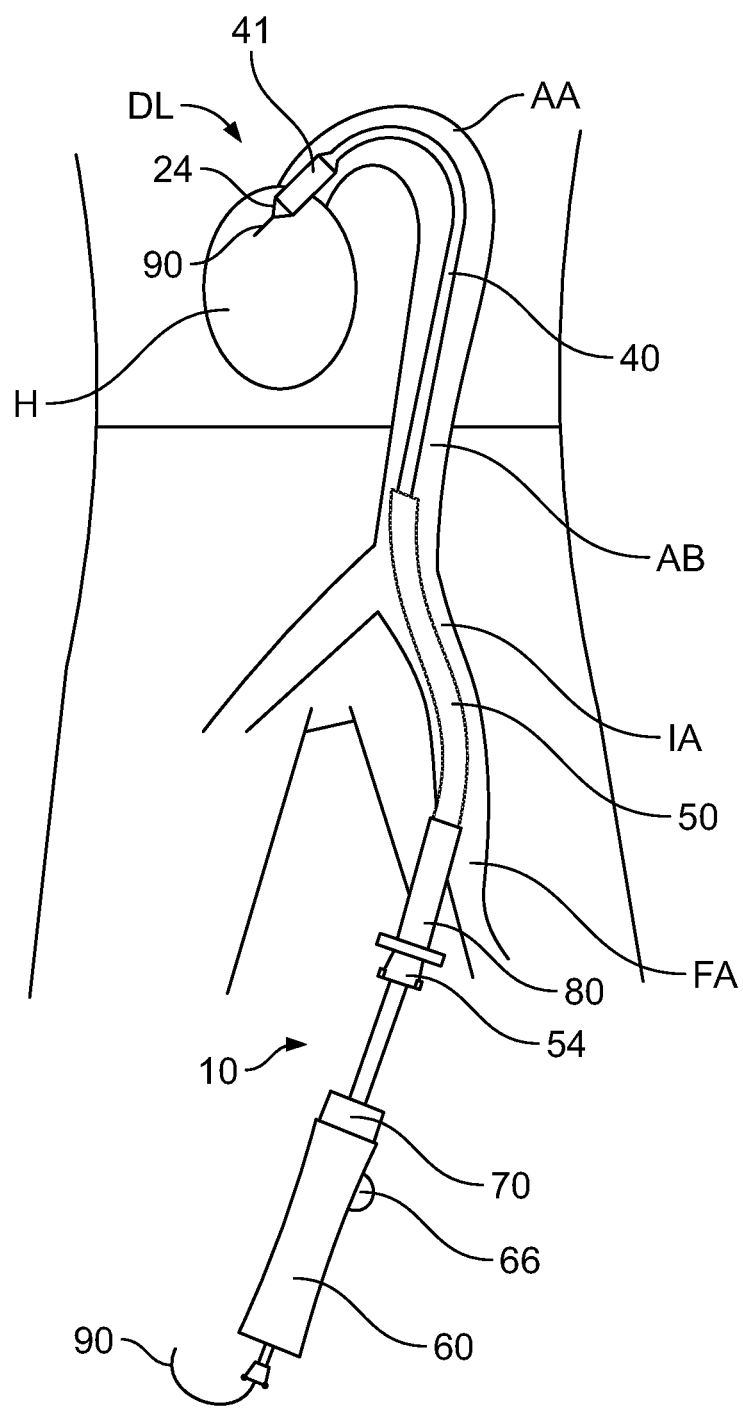
FIG. 9 is a diagrammatic view depicting the delivery system of FIG. 1 and introducer of FIG. 8 in use in a human patient.

Referring to FIG. 9, in a method of operation according to a further aspect of the disclosure, an implantable device such as a prosthetic heart valve is implanted in a subject at a location DL that is in the vicinity of the aortic annulus of the subject's heart H. To prepare for performing the method, introducer 80 is inserted into the subject's femoral artery FA through an entry site at the subject's groin, using a conventional technique, such as the Seldinger technique. A guidewire 90 is inserted through introducer 80 and advanced through femoral artery FA, iliac artery IA and abdominal aorta AB, around aortic arch AA, and through the aortic annulus into heart H.

The implantable device and delivery device 10 are brought to the condition shown in FIG. 1, with outer shaft 40 and sheath 41 in their fully advanced position relative to inner shaft 20 so that sheath 41 covers the implantable device, and with sleeve 50 in its fully advanced position, abutting the rim 45 in the proximal structure 44 of the sheath. With device 10 in this condition, the device is threaded over the proximal end of guidewire 90 so that the proximal end of the guidewire enters the distal end of the lumen 26 in inner shaft 20 through tip 24. The physician grasps handle 60 and advances delivery device 10 into the vasculature through introducer 80 with tip 24 leading. During the initial stages of the advancement, the physician maintains sleeve 50 in its fully advanced condition and engaged with sheath 41, for example, by grasping the hub 54 of sleeve 50 and urging the sleeve forward. The physician may also apply distally directed force to handle 60. The smooth transition between the outer surfaces of outer sheath 41 and sleeve 50 facilitates insertion of the sleeve through the elastomeric seal 82 of introducer 80. The physician may continue to advance delivery device 10 through the subject's vasculature with sleeve 50 in its fully advanced position relative to sheath 41 until the hub 54 of the sleeve is disposed adjacent introducer 80.

When the hub 54 of sleeve 50 encounters introducer 80, forward movement of the sleeve is stopped. At this point, based on the length of sleeve 50, the distal end of sleeve 50 will be disposed in abdominal aorta AB, remote from aortic arch AA. The physician may continue to advance inner shaft 20 and outer shaft 40 simultaneously by advancing handle 60. During such advancement, outer shaft 40 slides readily through sleeve 50. By the time tip 24 at the distal end of delivery device 10 approaches aortic arch AA, a substantial portion of outer shaft 40 will be disposed distally of sleeve 50. This portion of outer shaft 40 can bend readily because it is not constrained by sleeve 50. Thus, delivery device 10 can follow or "track" guidewire 90 as it traverses the bend of aortic arch AA. Continued advancement brings sheath 41 and the device-carrying region 28 of inner shaft 20 to the desired delivery location DL, near the aortic annulus. The ability of outer shaft 40 to readily slide within sleeve 50 facilitates precise positioning at delivery location DL. The physician typically confirms proper positioning by fluoroscopic imaging and makes any necessary adjustments. At this stage of the procedure, the hub 54 of sleeve 50 typically is spaced distally from the catch 70 on handle 60, as depicted in FIG. 9. Stated another way, sleeve 50 is in a partially retracted position relative to inner shaft 20 and outer shaft 40.

While holding handle 60 steady to maintain the position of the implantable device, the physician can grasp sleeve 50, such as by grasping hub 54, and can pull the hub and sleeve proximally to bring the sleeve to its fully retracted position against catch 70, and can then engage the projections 56 on the hub with the internal threads 74 of the catch to connect the hub to the catch. Although introducer 80 and the tissues of the subject bearing on sleeve 50 exert appreciable frictional forces on the sleeve, the sleeve slides relatively freely over outer shaft 40 of delivery device 10. Once hub 54 is connected to catch 70, handle 60 is locked to sleeve 50. In embodiments where handle 60 does not include catch 70, the hub 54 does not lockingly engage handle 60 and may be left in position adjacent the access site in the patient during the procedure.

After locking handle 60 to sleeve 50, the physician operates control element 66 to retract outer shaft 40 relative to inner shaft 20 and relative to the implantable device. The physician holds handle 60 steady during this step to assure that inner shaft 20 and the implantable device remain stationary while outer shaft 40 and sheath 41 move relative to the patient. The frictional forces exerted on sleeve 50 by the seal 82 of introducer 80 and by tissues in contact with the sleeve help to keep the handle stationary. This is opposite what would occur if delivery device 10 was used without sleeve 50, with outer shaft 40 in direct contact with the seal 82 of introducer 80. In that case, the frictional forces exerted by introducer seal 82 and the tissues adjacent the entry site would tend to hold outer shaft 40 stationary, and operation of control element 66 would tend to cause inner shaft 20 and handle 60 to move relative to the patient, thereby moving the implantable device away from its desired position.

The procedure described above can be varied. For example, while delivery device 10 is being advanced to delivery location DL, the physician can stop the distal movement of sleeve 50 before hub 54 encounters introducer 80. Also, the physician can retract sleeve 50 during advancement of the delivery device. Either of these approaches will leave the distal end of sleeve 50 lower in abdominal aorta AB or in iliac artery IA while tip 24 and sheath 41 traverse aortic arch AA. This in turn further increases the flexibility of the leading portion of outer shaft 40 for tracking along guidewire 90 through aortic arch AA, since a greater length of outer shaft 40 is exposed.

Figure 10:
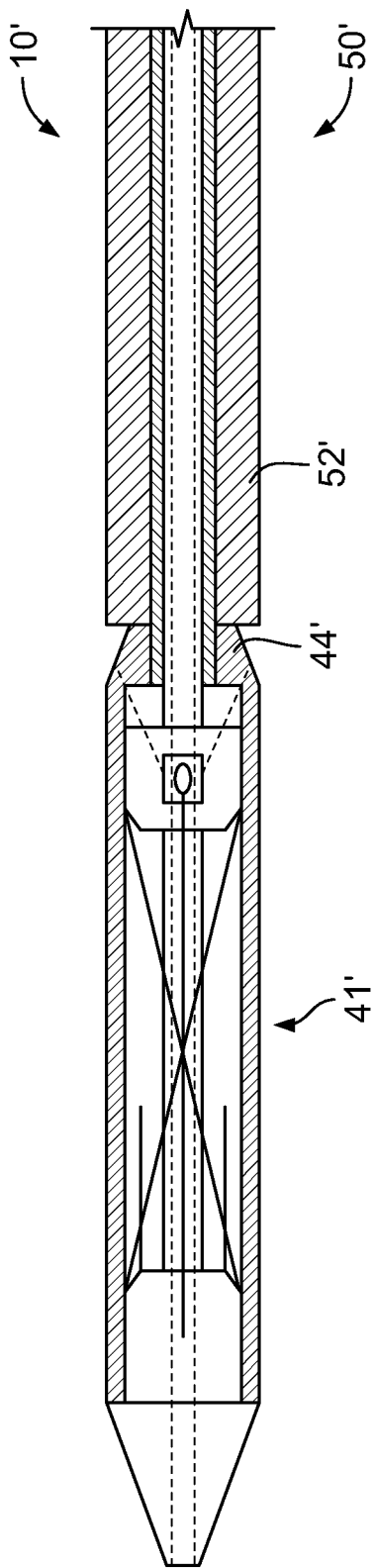
FIGS. 10-12 are cross-sectional views of the distal end of a delivery system of the prior art in different operating positions.
Figure 11:
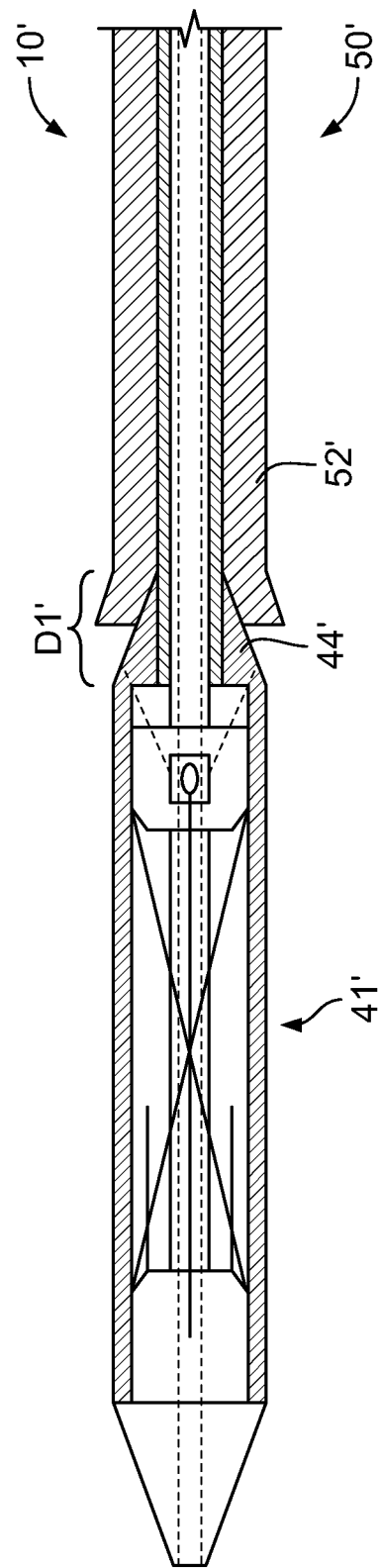
Figure 12:
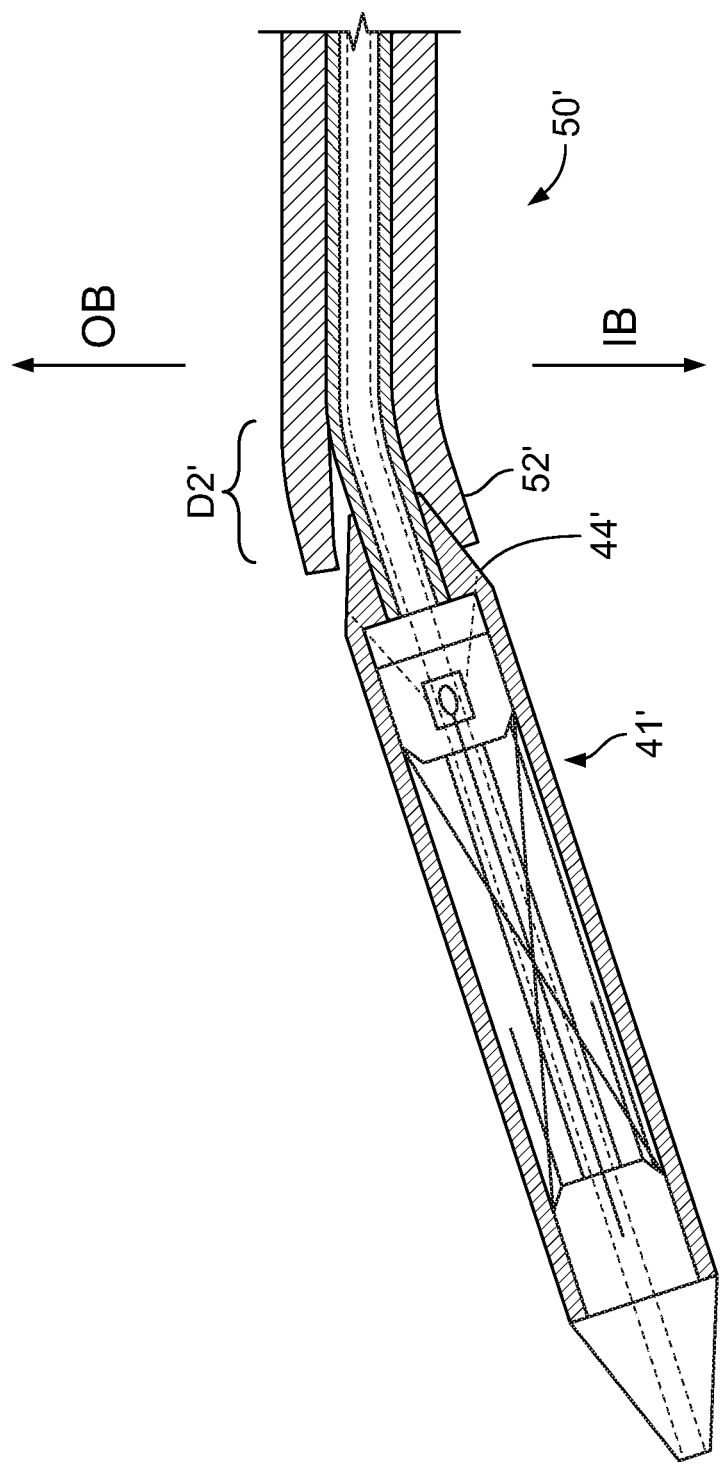

The engagement between sleeve 50 and the landing zone 44b of the proximal structure 44 of sheath 41 facilitates advancement of delivery device 10 and minimizes trauma to the vasculature, particularly in comparison to certain prior delivery devices. In certain prior art devices having a ramped transition between a sleeve similar to sleeve 50 and a sheath similar to sheath 41, the ramped transition is entirely conical or frustoconical, without a landing zone described in the present disclosure. The distal end of such a prior art delivery device 10' having a conical transition 44' is illustrated in FIG. 10. Delivery device 10' may include an integrated sheath or sleeve 50' having a substantially cylindrical opening at its distal end 52'. When sleeve 50' is engaged over conical transition 44' a smooth transition is not created, resulting in potential drawbacks as delivery device 10' is advanced through the vasculature. A first potential drawback is that with the distal end 52' of sleeve 50' engaged over the conical transition 44' of sheath 41', the geometries of the components may increase the likelihood of the cylindrical opening of the sleeve deforming outwardly or expanding when distal forces are applied to the sleeve to advance delivery device 10' through the vasculature. This deformation occurs because there is no positive stop (such as rim 45 on delivery device 10) preventing sleeve 50' from moving further distally relative to sheath 41' as advancement forces are applied to the sleeve. This type of deformation or expansion is indicated at D1' in FIG. 11, and may result in sharp edges that could cause damage to the tissue of the patient. A second potential drawback is that, with the distal end 52' of sleeve 50' engaged over conical transition 44' of sheath 41', the area of engagement between those components is small. As a result, during insertion of delivery device 10' into the vasculature, and particularly as sleeve 50' and sheath 41' "track" or otherwise bend along the curves of the vasculature, the distal end 52' of sleeve 50' may separate from the conical transition 44' of sheath 41'. In other words, as sheath 41' bends or flexes relative to sleeve 50', transition 44' may compress the sleeve wall near the inside bend IB of the vasculature while separating from the sleeve wall near the outside bend OB of the vasculature. This scenario may also result in a deformation zone, indicated at D2' in FIG. 12, with sharp edges of sleeve 50' being exposed to potentially damage the vasculature, for example by scraping the patient's tissue as sleeve 50' and sheath 41' traverse the outside bend OB of the vasculature.

Unlike sheath 41' and sleeve 50' shown in FIG. 10, the proximal structure 44 of sheath 41 includes a cylindrical landing zone 44b, as described above. When the distal end portion 52 of sleeve 50 is in the fully advanced position, there is a relatively long length of engagement between the inner diameter of the sleeve and the outer surface of landing zone 44b. This increased length of engagement may help resist separation between the distal portion 52 of sleeve 50 and the proximal structure 44 of sheath 41 as delivery device 10 bends along tortuous anatomy, such as that shown in FIG. 12. Further, the engagement of the distalmost end of sleeve 50 with the rim 45 in the proximal structure 44 of sheath 41 may prevent distal movement of the sleeve relative to the sheath causing the type of deformation shown in FIG. 11.

In a method according to a further aspect of the disclosure, delivery device 10 may be inserted without placing an introducer at the entry location. Methods according to this variant are generally the same as the methods for inserting delivery device 10 described above. Here again, sleeve 50 desirably is at its advanced position when delivery device 10 is inserted into femoral artery FA after placement of guidewire 90. The smooth transition between the outer surface of sheath 41 and the outer surface of sleeve 50 facilitates advancement of the delivery device through the tissue at the entry location, and helps to minimize trauma. Moreover, when sleeve 50 is in its advanced position, it acts to stiffen the leading portion of the delivery device. This makes it easier to force the delivery device through the tissue at the entry location. The physician may grasp sleeve 50 at hub 54 or at another location and urge the sleeve forward during insertion into femoral artery FA, thus forcing sheath 41, inner shaft 20 and outer shaft 40 distally.

The advancement of delivery device 10 is continued at least until the front end of sleeve 50 enters femoral artery FA. The physician may continue moving sleeve 50 distally until the hub 54 of the sleeve reaches the patient's skin, or may stop moving the sleeve distally when it has reached a desired location. After the implantable device has reached the desired delivery location, sleeve 50 desirably is retracted and locked to the catch 70 on handle 60. Because sleeve 50 is forcibly engaged by tissue at the entry location, the sleeve will again help to hold handle 60 and inner shaft 20 stationary while sheath 41 is retracted to expose the implantable device. However, in embodiments in which handle 60 does not include catch 70, hub 54 may remain positioned at or adjacent the patient's skin during the procedure until delivery device 10 is removed from the patient.

Omission of introducer 80 enables use of both a larger diameter sheath 41 and a larger sleeve 50 in an artery of a given size at the entry location. Where an introducer 80 is used, the introducer must have an outside diameter small enough to fit within femoral artery FA at the entry location. As the diameters of sheath 41 and sleeve 50 must be less than the inside diameter of introducer 80 to allow for easy sliding movement therebetween, the diameters of the sheath and sleeve are somewhat limited. Where introducer 80 is omitted, the diameters of the sheath 41 and sleeve 50 are limited only by the diameter of the arteries.

In the embodiments discussed above, the implantable device is self-expanding. However, in other embodiments a balloon or other expandable element is provided on inner shaft 20 in device-carrying region 28, and is used to expand the implantable device after retraction of the sheath.

According to a first aspect of the disclosure, a delivery device for an implantable medical device comprises:

(a) an elongated inner shaft having a distal end and a device-carrying region adjacent the distal end;

(b) an elongated, hollow outer shaft surrounding the inner shaft, the outer shaft having a distal end and being slideable relative to the inner shaft;

(c) a sheath at the distal end of the outer shaft and slideable with the outer shaft, a main portion of the sheath having an outside diameter greater than an outside diameter of the outer shaft, the outer shaft being movable relative to the inner shaft in a proximal direction from an advanced position in which the sheath surrounds the device-carrying region of the inner shaft to a retracted position in which the sheath exposes the device-carrying region, the sheath having a proximal structure including (i) a cylindrical portion, (ii) a first transition zone extending between the outer shaft and the cylindrical portion, and (iii) a second transition zone extending between the cylindrical portion and the main portion of the sheath; and (d) a sleeve surrounding a portion of the outer shaft and being moveable relative to the outer shaft from an advanced position in which a distal end portion of the sleeve surrounds the cylindrical portion of the proximal structure of the sheath to a retracted position in which the distal end of the sleeve is spaced proximally from the cylindrical portion of the proximal structure of the sheath; and/or the distal end of the sleeve has an outside diameter substantially equal to an outside diameter of the main portion of the sheath; and/or the sheath and the distal end of the sleeve are concentric with one another when the sleeve is in the advanced position; and/or a proximal end of the second transition zone has a diameter greater than a diameter of a distal end of the cylindrical portion so as to define an annular rim in the proximal structure; and/or a distalmost end of the sleeve abuts the annular rim when the sleeve is in the advanced position; and/or the distal end portion of the sleeve has an outer diameter that tapers inwardly in the distal direction; and/or a distalmost end of the sleeve has an outer diameter that is substantially equal to the diameter of the annular rim; and/or the first transition zone and second transition zone each have a conical or frustoconical shape; and/or a handle including a housing and a control element projecting from the housing, the inner shaft being fixedly connected to the housing and the outer shaft being moveable relative to the inner shaft in response to operation of the control element; and/or the distal end portion of the sleeve and the second transition zone cooperatively define a smooth exterior surface when the sleeve is in the advanced position.

According to a second aspect of the disclosure, a method of delivering an implantable medical device into the vasculature of a patient comprises:

(a) advancing a delivery device into the vasculature of the patient at an entry location, the delivery device including an inner shaft having a distal end and a device-carrying region adjacent the distal end, an implantable device mounted in the device-carrying region, a hollow outer shaft surrounding the inner shaft, the outer shaft having a distal end, a sheath at the distal end of the outer shaft, and a sleeve surrounding a portion of the outer shaft, the sheath having a proximal structure including a cylindrical portion, the advancing being performed while a distal end portion of the sleeve surrounds the cylindrical portion of the proximal structure of the sheath and at least until the distal end portion of the sleeve enters the vasculature;

(b) sliding the outer shaft and the inner shaft relative to the sleeve to advance the outer shaft and inner shaft portion into the vasculature; and (c) retracting the outer shaft and the sheath relative to the sleeve and relative to the inner shaft to expose the implantable device; and/or the advancing step includes sliding the sheath and the sleeve through an introducer disposed at the entry location and through a resilient hemostatic seal mounted in the introducer; and/or the advancing step includes sliding the sheath and the sleeve through tissues of the subject at the entry location so that the sleeve and sheath contact the tissues; and/or the proximal structure of the sheath includes a first transition zone extending between the outer shaft and the cylindrical portion, and a second transition zone extending between the cylindrical portion and a main portion of the sheath, the main portion of the sheath having an outer diameter substantially equal to an outer diameter of the sleeve; and/or the distal end portion of the sleeve and a proximal end of the second transition zone cooperatively define a smooth exterior surface during the advancing step; and/or a proximal end of the second transition zone has a diameter greater than a diameter of a distal end of the cylindrical portion so as to define an annular rim in the proximal structure; and/or prior to the advancing step, the sleeve is advanced relative to the sheath until a distalmost end of the sleeve contacts the annular rim; and/or the distalmost end of the sleeve has an outer diameter that is substantially equal to a diameter of the annular rim; and/or the advancing step includes advancing the sheath around a bend in a blood vessel with the distal end portion of the sleeve surrounding the cylindrical portion of the proximal structure of the sheath.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing form the spirit and scope of the present invention as defined by the appended claims.

The invention claimed is:

1. A delivery device for an implantable medical device, the delivery device comprising:
   (a) an elongated inner shaft having a distal end and a device-carrying region adjacent the distal end;
   (b) an elongated, hollow outer shaft surrounding the inner shaft, the outer shaft having a distal end and being slideable relative to the inner shaft;
   (c) a sheath at the distal end of the outer shaft and slideable with the outer shaft, a main portion of the sheath having an outside diameter greater than an outside diameter of the outer shaft, the outer shaft being movable relative to the inner shaft in a proximal direction from an advanced position in which the sheath surrounds the device-carrying region of the inner shaft to a retracted position in which the sheath exposes the device-carrying region, the sheath having a proximal structure including (i) a cylindrical portion, (ii) a first transition zone extending between the outer shaft and the cylindrical portion, and (iii) a second transition zone extending between the cylindrical portion and the main portion of the sheath; and
   (d) a sleeve surrounding a portion of the outer shaft and being moveable relative to the outer shaft from an advanced position in which a distal end portion of the sleeve surrounds the cylindrical portion of the proximal structure of the sheath to a retracted position in which the distal end of the sleeve is spaced proximally from the cylindrical portion of the proximal structure of the sheath.

2. The delivery device of claim 1, wherein the distal end of the sleeve has an outside diameter substantially equal to an outside diameter of the main portion of the sheath.

3. The delivery device of claim 2, wherein the sheath and the distal end of the sleeve are concentric with one another when the sleeve is in the advanced position.

4. The delivery device of claim 1, wherein a proximal end of the second transition zone has a diameter greater than a diameter of a distal end of the cylindrical portion so as to define an annular rim in the proximal structure.

5. The delivery device of claim 4, wherein a distalmost end of the sleeve abuts the annular rim when the sleeve is in the advanced position.

6. The delivery device of claim 4, wherein the distal end portion of the sleeve has an outer diameter that tapers inwardly in the distal direction.

7. The delivery device of claim 6, wherein a distalmost end of the sleeve has an outer diameter that is substantially equal to the diameter of the annular rim.

8. The delivery device of claim 1, wherein the first transition zone and second transition zone each have a conical or frustoconical shape.

9. The delivery device of claim 1, further comprising a handle including a housing and a control element projecting from the housing, the inner shaft being fixedly connected to the housing and the outer shaft being moveable relative to the inner shaft in response to operation of the control element.

10. The delivery device of claim 1, wherein the distal end portion of the sleeve and the second transition zone cooperatively define a smooth exterior surface when the sleeve is in the advanced position.

11. The delivery device of claim 1, wherein, in the advanced position, the sleeve surrounds the first transition zone, and
the cylindrical portion is sandwiched between the outer tube and the sleeve.

12. A method of delivering an implantable medical device into the vasculature of a patient, comprising:
(a) advancing a delivery device into the vasculature of the patient at an entry location, the delivery device including an inner shaft having a distal end and a device-carrying region adjacent the distal end, an implantable device mounted in the device-carrying region, a hollow outer shaft surrounding the inner shaft, the outer shaft having a distal end, a sheath at the distal end of the outer shaft, and a sleeve surrounding a portion of the outer shaft, the sheath having a proximal structure including a cylindrical portion, the advancing being performed while a distal end portion of the sleeve surrounds the cylindrical portion of the proximal structure of the sheath and at least until the distal end portion of the sleeve enters the vasculature;
(b) sliding the outer shaft and the inner shaft relative to the sleeve to advance the outer shaft and inner shaft portion into the vasculature; and
(c) retracting the outer shaft and the sheath relative to the sleeve and relative to the inner shaft to expose the implantable device.

13. The method of claim 12, wherein the advancing step includes sliding the sheath and the sleeve through an introducer disposed at the entry location and through a resilient hemostatic seal mounted in the introducer.

14. The method of claim 12, wherein the advancing step includes sliding the sheath and the sleeve through tissues of the subject at the entry location so that the sleeve and sheath contact the tissues.

15. The method of claim 12, wherein the proximal structure of the sheath includes a first transition zone extending between the outer shaft and the cylindrical portion, and a second transition zone extending between the cylindrical portion and a main portion of the sheath, the main portion of the sheath having an outer diameter substantially equal to an outer diameter of the sleeve.

16. The method of claim 15, wherein the distal end portion of the sleeve and a proximal end of the second transition zone cooperatively define a smooth exterior surface during the advancing step.

17. The method of claim 15, wherein a proximal end of the second transition zone has a diameter greater than a diameter of a distal end of the cylindrical portion so as to define an annular rim in the proximal structure.

18. The method of claim 17, wherein, prior to the advancing step, the sleeve is advanced relative to the sheath until a distalmost end of the sleeve contacts the annular rim.

19. The method of claim 18, wherein the distalmost end of the sleeve has an outer diameter that is substantially equal to a diameter of the annular rim.

20. The method of claim 12, wherein the advancing step includes advancing the sheath around a bend in a blood vessel with the distal end portion of the sleeve surrounding the cylindrical portion of the proximal structure of the sheath.

* * * * *